United States Patent
Maus et al.

(10) Patent No.: US 9,416,426 B2
(45) Date of Patent: *Aug. 16, 2016

(54) ASSAY FOR CHLAMYDIA TRACHOMATIS BY AMPLIFICATION AND DETECTION OF CHLAMYDIA TRACHOMATIS PMPA GENE

(71) Applicant: Becton, Dickinson and Company, Franklin Lakes, NJ (US)

(72) Inventors: Courtney E. Maus, Pasadena, MD (US); Jason P. Stevens, Owings Mills, MD (US); Danielle Koffenberger, Stewartstown, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 523 days.

This patent is subject to a terminal disclaimer.

(21) Appl. No.: 13/786,994

(22) Filed: Mar. 6, 2013

(65) Prior Publication Data

US 2013/0274122 A1 Oct. 17, 2013

Related U.S. Application Data

(63) Continuation-in-part of application No. 12/605,515, filed on Oct. 26, 2009, now Pat. No. 8,492,092.

(60) Provisional application No. 61/197,429, filed on Oct. 27, 2008.

(51) Int. Cl.
*C12P 19/34* (2006.01)
*C12Q 1/68* (2006.01)

(52) U.S. Cl.
CPC ............ *C12Q 1/689* (2013.01); *C12Q 2600/16* (2013.01)

(58) Field of Classification Search
USPC .................... 435/6.12, 91.2; 536/24.32, 24.33
See application file for complete search history.

(56) References Cited

U.S. PATENT DOCUMENTS

| 5,470,723 | A | 11/1995 | Walker et al. |
| 5,538,870 | A | 7/1996 | Noeth et al. |
| 5,928,869 | A | 7/1999 | Nadeau et al. |
| 5,958,700 | A | 9/1999 | Nadeau et al. |
| 6,448,234 | B1 | 9/2002 | Fling |
| 7,601,491 | B2 | 10/2009 | Collis et al. |
| 2005/0106162 | A1 | 5/2005 | Grandi et al. |
| 2007/0065837 | A1 | 3/2007 | Eickhoff et al. |
| 2007/0269810 | A1 | 11/2007 | Trama et al. |
| 2009/0042814 | A1 | 2/2009 | Petyaev et al. |

FOREIGN PATENT DOCUMENTS

| EP | 0915172 A2 | 5/1999 |
| WO | 2006050571 A1 | 5/2006 |
| WO | 2007042827 A2 | 4/2007 |

OTHER PUBLICATIONS

Walker et al., "Strand desplacement amplification—an asothermal, in vitro DNA amplification technique", Nucleic Acids Research, Vo. 20, No. 7, 1691-1696, 1992.
Alexander Sarah et al: itA comparison of two methods for the diagnosis of lymphogranuloma venereum. Journal of Medical Microbiology Aug. 2008, vol. 57, No. Pt 8, Aug. 2008, pp. 962-965, ISSN: 0022-2615.
Goldschmidt P et al: "Detection by broad-range real-time PCR assay of *Chlamydia* species infecting human and animals" British Journal of Ophthalmology, vol. 90, No. 11, Nov. 2006, pp. 1425-1429, ISSN: 0007-1161.
Gomes Joao P et al: "Polymorph isms in the nine polymorphic membrane proteins of Chlamydia trachomatis across all serovars: Evidence for serovar Da recombination and correlation with tissue tropism" Journal of Bacteriology, American Society for Microbiology, US, vol. 188, No. 1, Jan. 1, 2006, pp. 275-286, XP002455404 ISSN: 0021-9193.
International Search Report and Written Opinion, PCT/US2009/005856, dated Feb. 5, 2010.
Jennings et al., "Recommended principles and practices for validating clinical molecular pathology tests", Arch Pathol Lab Med, vol. 133, pp. 743-755, May 2009.
Magbanua et al., "Chlamydia trachomatis variant not detected by plasmid-based nucleic acid amplification tests: Molecular characterisation and failure of single dose azithromycin", STI Online First, Published Jun. 13, 2007.
Ripa et al., "A Chlamydia trachomatis strain with a 377-bp deletion in the cryptic plasmid causing false-negative nucleic acid amplification tests", Sexually Transmitted Diseases, May 2007, vol. 34, No. 5, p. 255-256.
Rychlik et al., Nucleic Acids Research 17(21), 8543-8551 (1989).

*Primary Examiner* — Kenneth Horlick
(74) *Attorney, Agent, or Firm* — Lerner, David, Littenberg, Krumholz & Mentlik, LLP

(57) ABSTRACT

A region of the *Chlamydia trachomatis* pmpA gene has been identified which is useful for performing amplification assays to determine specifically whether *C. trachomatis* is present in the sample being tested. Oligonucleotides useful for detecting this gene by performing the polymerase chain reaction (PCR) are disclosed. The disclosed oligonucleotides can be used in an assay which is specific for multiple strains or serovars of *C. trachomatis*, including the variant E serovar, and which does not show cross reactivity with the genomes of other microorganisms or with human DNA. In addition, the disclosed oligonucleotides can be used to in a multiplex system. This invention also contemplates a kit including oligonucleotides, and optionally other reagents, for the detection of *C. trachomatis* using PCR.

33 Claims, 1 Drawing Sheet

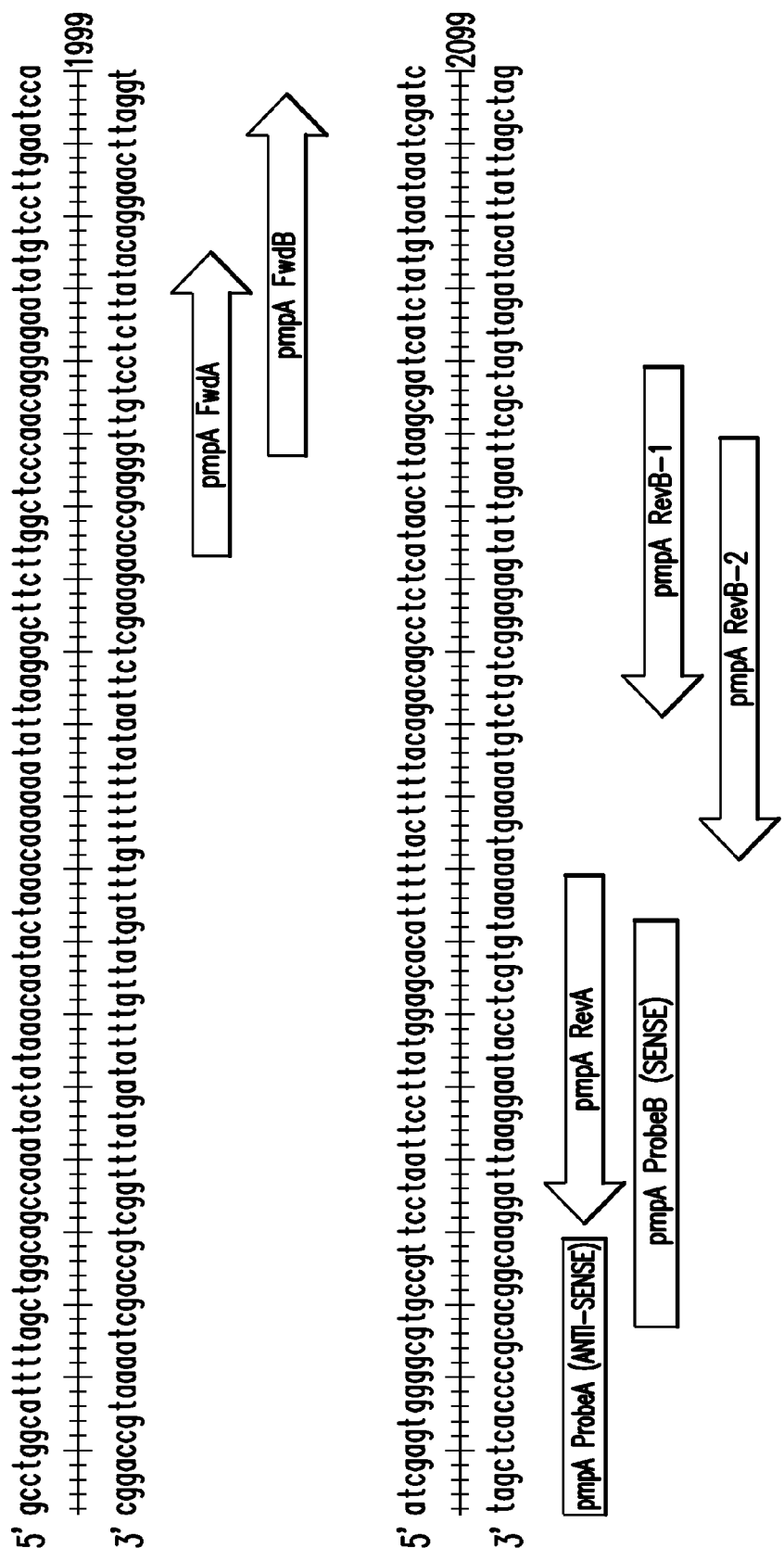

ASSAY FOR CHLAMYDIA TRACHOMATIS BY AMPLIFICATION AND DETECTION OF CHLAMYDIA TRACHOMATIS PMPA GENE

CROSS-REFERENCE TO RELATED APPLICATIONS

This application is a continuation-in-part of U.S. patent application Ser. No. 12/605,515, filed Oct. 26, 2009, which issued as U.S. Pat. No. 8,492,092, which application claims the benefit of the filing date of U.S. Provisional Patent Application No. 61/197,429 filed Oct. 27, 2008, the disclosures of which are hereby incorporated herein by reference.

SEQUENCE LISTING

The instant application contains a substitute Sequence Listing which has been submitted in ASCII format via EFS-Web and is hereby incorporated by reference in its entirety. Said ASCII copy, created on Jun. 25, 2013, is named Sequence Listing for Chlamydia Trachomatis (2)_ST25.txt and is 8,731 bytes in size.

BACKGROUND OF THE INVENTION

Chlamydia trachomatis (C. trachomatis) is a prokaryote. This organism includes the A, B, Ba, C, D, E, variant E, F, G, H, I, J, K, LGVI, LGVII, and LGVIII serotypes. C. trachomatis is the causative agent of trachoma (which is the greatest single cause of preventable blindness worldwide), inclusion conjunctivitis, infant pneumonitis, urethritis and lymphogranuloma venereum. Diagnosis and detection of this organism is often on the basis of pathologic or clinical findings and may be confirmed by isolation and staining techniques.

The genome of C. trachomatis includes a cryptic plasmid which is approximately 7.5 kb in size and is present in multiple copies in the organism. The presence of multiple copies makes this plasmid a good target for diagnostic assays using nucleic acid amplification techniques, such as Polymerase Chain Reaction (PCR) and Strand Displacement Amplification (SDA). Accordingly, many diagnostic companies currently manufacture DNA amplification assays that use the organism's cryptic plasmid as a target for detecting C. trachomatis in a biological sample.

However, there have been reports of C. trachomatis lacking the cryptic plasmid and such strains have been isolated from patients. Additionally, there have been reports of a variant strain of C. trachomatis, variant E, harboring a cryptic plasmid with a 377 base pair deletion, the area of which is targeted by assays used to detect C. trachomatis. Assays that target this area would therefore yield a false-negative result. Thus, new diagnostic techniques aimed at more reliably and accurately detecting C. trachomatis are desired.

A multi-plex DNA amplification reaction is a process in which several target genes are amplified and detected in a single reaction. This allows for the rapid screening and/or detection of multiple genes/organisms within a sample using a single assay. In a multi-plexing platform, a single reaction mixture is prepared with all reagents needed to amplify and detect each gene of interest. Often, however, these multiple reagents can cross-react with each other negatively affecting, or inhibiting, the amplification reacting and lead to false negative results. In addition, one particular amplification reaction within the mix of reactions may be more efficient than the other reactions and may consume certain reagents, such as nucleotides, at a faster rate limiting the availability of those reagents to the other assays in later amplification cycles. Accordingly, there is a need for rapid methods and reagents that allow for the detection of C. trachomatis that would also allow for the amplification and detection of multiple genes/organisms in a single assay format.

Another challenge associated with amplification reactions is that the DNA sample to be amplified must be extracted from the microorganism in the sample prior to amplification and detection. Current methods of isolating DNA from the organism in a sample involve multiple extraction steps that cause a delay in identification the microorganism in the biological sample. The multiple extraction steps are often required because the extraction buffers are incompatible with the amplification reaction and need to be removed from the sample prior to amplification and detection. Accordingly, there is need for rapid methods and reagents for extracting DNA from the microorganism in the sample in a manner in which the extraction reagents do not interfere with the downstream amplification reaction.

SUMMARY OF THE INVENTION

Oligonucleotides described herein may be used to detect the presence of C. trachomatis in a sample by amplification and detection of the pmpA gene. More specifically, the oligonucleotides described herein may be used to amplify one or more portions of the pmpA nucleic acid sequence within the organism. Even more specifically, the oligonucleotides described herein target a portion, base pairs 1835-2176 of Genbank Accession AY884095, of the C. trachomatis pmpA gene. The relevant portion of the pmpA gene is illustrated in FIG. 1. In one embodiment, the oligonucleotides described herein target base pairs 1966-2078 of the pmpA gene.

In one embodiment, the biological sample is a clinical sample. Types of clinical samples contemplated included, for example, blood samples, urine samples, vaginal swabs, endocervical swabs, urethral swabs, and liquid-based cytology samples.

In one embodiment, methods and reagents are contemplated that utilize a lysis buffer for lysing the microorganism prior to amplification and detection of the target gene. In this embodiment, the lysis buffer may contain a non-ionic detergent, such as for example, Tween®-20, and optionally an organic solvent.

In another embodiment, the methods described herein include treating a sample using one or more oligonucleotides specific for the target sequence in a nucleic acid amplification reaction and detecting the presence or absence of the amplified nucleic acid product using PCR, e.g., end-point PCR or real-time PCR such as Taqman® real-time PCR.

Although the target region of the pmpA gene is generally about base pairs 1835-2176 as noted above, in certain embodiments the oligonucleotide primers and probes bind to the pmpA gene region at a location of the gene that is between about base pair 1966 to about base pair 2078. Primer/probe sets are configured to not only selectively bind in this region of the pmpA gene, but to amplify some portion of the pmpA gene sequence for detection. The oligonucleotides described herein may also be used, either alone or in combination, to facilitate detection through amplification of pmpA gene nucleic acid sequence.

One example of specific binding sites on the pmpA gene for specific exemplary PCR primers and probes is listed in the following Table 1 identified by their nucleotide sequence along with their location on the target region of the pmpA gene.

TABLE 1 pmpA BINDING SITES FOR PCR PRIMERS

| SEQUENCE (5' to 3') | LOCATION* | SEQ ID NUMBER |
|---|---|---|
| ATA TTC TCC TGT TGG GAG CCA | 1966-1986 | SEQ ID NO: 3 |
| CCT AAT TCC TTA TGG AGC ACA TTT | 2020-2043 | SEQ ID NO: 4 |
| ATC GAG TGG GGC GTG CCG T | 2000-2018 | SEQ ID NO: 5 |
| GAT TCA AGG ACA TAT TCT CCT GTT G | 1973-1997 | SEQ ID NO: 6 |
| GAC AGC CTC TCA TAA CTT AAG CGA | 2055-2078 | SEQ ID NO: 7 |
| TGT GCT CCA TAA GGA ATT AGG AAC GGC A | 2013-2040 | SEQ ID NO: 8 |
| TAC TTT TAC AGA CAG CCT CTC ATA ACT TA | 2045-2073 | SEQ ID NO: 9 |

*Genbank Accession AY884095

The oligonucleotide PCR primers and probes described herein are sufficiently complementary to the target region of the pmpA gene as to selectively bind to those regions. As described in detail below, the primers and probes are at least 70% complementary with the target. Given that the invention contemplates less than complete complementarity between primer/probe and target, the skilled person can vary both the location of a specific primer or probe on the target region, and the length and sequence of the specific primers and probes to achieve the objectives of the assay for which the primers and probes are designed. Examples of primers and probes used for Taqman® real-time PCR assays, described in terms of their oligonucleotide sequences, are:

TABLE 2

Taqman® real-time PCR Primers and Probes

| Description: | Sequence (5' to 3') | SEG ID Number |
|---|---|---|
| Forward Primer A | TGG CTC CCA ACA GGA GAA TAT | SEQ ID NO: 10 |
| Reverse Primer A | AAA TGT GCT CCA TAA GGA ATT AGG | SEQ ID NO: 11 |
| Probe A | ACG GCA CGC CCC ACT CGA T | SEQ ID NO: 12 |
| Forward Primer B | CAA CAG GAG AAT ATG TCC TTG AAT C | SEQ ID NO: 13 |
| Reverse Primer B-1 | TCG CTT AAG TTA TGA GAG GCT GTC | SEQ ID NO: 14 |
| Probe B | TGC CGT TCC TAA TTC CTT ATG GAG CAC A | SEQ ID NO: 15 |
| Reverse Primer B-2 | TAA GTT ATG AGA GGC TGT CTG TAA AAG TA | SEQ ID NO: 16 |

As described in Table 2 above, the oligonucleotide primers and probes are the perfect complement to the target binding sequences described in Table 1. In one embodiment the oligonucleotides used for amplification and detection of the target sequence contain two oligonucleotides for use as amplification primers and one oligonucleotide for use as a detector probe.

In one embodiment, the primers and probes described herein can be used in a multiplex amplification reaction in order to amplify and detect multiple genes/microorganisms simultaneously, without any negative effects on the amplification and detection on any of the target genes in the multiplex reaction.

In another embodiment, a kit is provided for the detection of C. trachomatis using PCR. The kit includes one or more of the oligonucleotide primers and probes described herein that selectively bind to the pmpA gene of C. trachomatis and are capable of amplifying a target sequence that may be used for detection of that organism. The kit is provided with one or more of the oligonucleotides and buffer reagents for performing amplification assays.

In one aspect of the kit, a set of oligonucleotide primers and probes and reagents for purposes of Taqman® real-time PCR may be provided. In this aspect, two oligonucleotides are provided as amplification primers and one oligonucleotide is provided for use as the detector probe.

In yet another aspect of the kit, the oligonucleotide primers and probes for Taqman® real-time PCR purposes, along with certain other reagents, may be provided in dried or liquid format. In dried format, the composition may be applied to an appropriate receptacle (e.g. microarray, microtiter plate, etc.) where sample and proper PCR buffers may be added to perform the assay.

BRIEF DESCRIPTION OF THE DRAWINGS

FIG. 1 illustrates three Taqman® oligonucleotide sets and the target binding sites to which the oligonucleotides attach in the target region of the pmpA gene (SEQ ID NO:2).

DETAILED DESCRIPTION

The polymorphic membrane proteins are distinctive to the Chlamydiales order and form a superfamily among species of Chlamydia. Prior studies indicate that the mean genetic difference is 0.1% for pmpA among all C. trachomatis serovars signifying that the pmpA gene is conserved and stable. The pmpA gene is known in the art and its sequence is about 3 kb in length. See Genbank Accession Number AY884095. There are nine *C. trachomatis* family members designated pmpA, pmpB, pmpC, pmpD, pmpE, pmpF, pmpG, pmpH, and pmpI. None appear to demonstrate homology with other bacteria. Thus, pmpA is advantageous for detection of *C. tractomatis* using the disclosed oligonucleotides designed to detect the pmpA gene because the likelihood of cross reaction/detection with other organisms or eukaryotic cells that could be found in a patient's sample is minimal. Without being bound by any theory Applicant believes that the pmpA gene encodes proteins associated with host cell adhesion and is a significant component of *C. trachomatis* pathogenesis.

Described herein is a method of detecting *C. trachomatis* using an assay that consists of one or more oligonucleotides that bind to the pmpA gene. More specifically, the oligonucleotides described herein target the region of base pairs 1835-2176 of the pmpA gene. The invention exploits the conservation and stability of the pmpA gene, along with its distinctiveness to Chlamydiaceae to minimize or eliminate cross reacting/detecting other organisms or eukaryotic cells. Oligonucleotides disclosed herein may be useful for identification of all serotypes of *C. trachomatis*. This includes, but is not limited to, the A, B, Ba, C, D, E, variant E, F, G, H, I, J, K, LGVI, LGVII, and LIII serotypes.

In one embodiment, methods and reagents are contemplated that utilize an extraction buffer for lysing the microorganism in the sample and extracting the DNA prior to amplification and detection of the target gene. In this embodiment, the extraction buffer may contain a non-ionic detergent. The detergent is compatible with the PCR reaction, i.e., the detergent does not interfere with hybridization of the oligonucleotides or amplification of the target region, and therefore does not need to be removed prior to amplification. In one embodiment, the non-ionic detergent is Tween®-20, Triton™ X-100, Triton™ X-114, Nonidet™ P-40, or combinations thereof.

In one embodiment a non-ionic detergent is added to the biological sample prior to the addition of the amplification reagents. After the sample containing non-ionic detergent is added to the amplification reaction mixture, reaction mixture is incubated at a high temperature, e.g. 95° C., to lyse the microorganism and extract the DNA prior to initiating the PCR reaction. In another embodiment the temperature range is about 85° C. to about 99° C. and the incubation time is up to about 30 minutes. In one embodiment the incubation at a high temperature occurs during the first cycle of the amplification reaction. In another embodiment, the incubation at a high temperature occurs as a separate step prior to initiating the amplification reaction. Lysing the organism using the methods and reagents described herein allows for accurate quantitation of *C. trachomatis* in the sample when performed in conjunction with the disclosed amplification and detection methods.

There is no limit to the concentration of the detergent when combined with the amplification reaction mixture. In one embodiment, the final concentration of the detergent is about 0.001% to about 4% volume by volume. In another embodiment the final concentration of the detergent in the amplification reaction buffer is about 0.02% to about 2% volume by volume. In yet another embodiment the final concentration of the detergent in the amplification reaction buffer is about 0.2% volume by volume.

In another embodiment, the extraction buffer additionally includes an organic solvent. Exemplary organic solvents may include dimethyl sulfoxide (DMSO) and formamide. There is no limit to the concentration of the organic solvent when combined with the amplification reaction mixture. In one embodiment, the final concentration of the organic solvent in the amplification reaction buffer is up to about 2.5% volume by volume.

The oligonucleotide primers and probe sets described herein are specifically designed to target the pmpA gene nucleic acid, and may be used for detecting *C. trachomatis* using PCR, e.g., end point PCR or real-time PCR such as Taqman® real-time PCR. The primers hybridize to and amplify a target region of the pmpA gene. The probe sets provide a detectable signal when the region targeted by the oligonucleotides is present in the sample. This is a highly reliable indication of the presence of the pmpA gene and, in turn, is a highly reliable indication for the presence of *C. trachomatis* in the sample. PCR generally, and Taqman® PCR specifically, are nucleic acid amplification techniques well known to those skilled in the art. As such, the more general aspects of these amplification techniques are not described in detail herein.

A PCR reaction typically uses two oligonucleotide amplification primers, a forward primer and a reverse primer, that hybridize to complimentary strands of the denatured DNA molecule and flank a template or target DNA sequence that is to be amplified. A primer mix may be prepared to contain the forward primer and the reverse primer. The primers may be used at final concentrations of about 0.5 μM to about 0.9 μM. An amplification primer is generally used for amplifying a target sequence by extension of the primer after hybridization to the target sequence. Amplification primers are typically about 10-150 nucleotides in length, preferably about 15-50 nucleotides in length. The total length of an amplification primer for use in PCR is typically about 20-50 nucleotides.

As a general guide in designing oligonucleotides useful as primers, melting temperature ($T_m$) decreases approximately 1° C.-1.5° C. with every 1% decrease in sequence homology. Temperature ranges may vary between about 50° C. and 62° C., but the amplification primers may be designed to be optimal at 52° C. Temperatures below 50° C. may result in primers lacking specificity, while temperatures over 62° C. may result in no hybridization. A further consideration when designing amplification primers may be the guanine and cytosine content. Generally, the GC content for a primer may be about 40% to 60%, but may also be less and can be adjusted appropriately by one skilled in the art. The hybridizing region of the target binding sequence may have a $T_m$ of about 50° C. to about 62° C. Annealing complementary and partially complementary nucleic acid sequences may be obtained by modifying annealing conditions to increase or decrease stringency (i.e., adjusting annealing temperature or salt content of the buffer). Modifications such as those to the disclosed sequences and any necessary adjustments of annealing conditions to maintain pmpA gene specificity require only routine experimentation and are within the ordinary skill in the art.

Elongation of the primers is catalyzed by a heat-stable DNA polymerase. A repetitive series of cycles involving template denaturation, primer annealing, and extension of the annealed primers by the polymerase results in an exponential accumulation of a specific DNA fragment.

There are three steps in an end-point PCR assay reaction. In step 1 of the cycle, the temperature is raised to about 95° C., and then the target DNA that is to be amplified is denatured into two separate strands. In step 2 of the cycle, the temperature is lowered to about 50° C. allowing primers to anneal to the single DNA strands. The primers are short oligomers that specifically attach to each of the two denatured DNA strands. In step 3 of the cycle, the temperature is raised to 72° C. degrees and a DNA polymerase enzyme extends the separated strands so that, after each cycle, for each double-stranded DNA, two copies of the double-stranded DNA are produced. These steps are repeated in each cycle in order to amplify target nucleic acid. For instance, the aforementioned steps of the PCR cycle may be repeated forty or more times.

The amplification products generated using the inventive primers may be detected by a characteristic size, for example on polyacrylamide or agarose gels stained with DNA intercalating agent, such as ethidium bromide. Alternatively, amplified C. trachomatis pmpA gene target sequence may be detected by means of an assay probe, which is an oligonucleotide tagged with a detectable label. In a further alternative a labeled amplification primer/internal probe is extended on the target sequence, as described by Walker et al., *Proc. Nat'l Acad. Sci. USA* 89:392 (1992); or Walker et al., *Nucl. Acids Res.* 20:1691 (1992). In another embodiment, detection is accomplished directly through hybridization and extension of a labeled reporter probe as described in U.S. Pat. No. 5,928,869 and U.S. Pat. No. 5,958,700. Preferably, the assay probe is selected to hybridize to a sequence in the target which is between the amplification primers, i.e., it should be an internal assay probe. Alternatively, an amplification primer sequence or the target binding sequence thereof may be used as the assay probe.

The detectable label of the assay probe may be a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Ligands are also useful for immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to or including such labels in, oligonucleotides are well known in the art and any of these methods are suitable for use in the invention described herein.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of two amplification primers), the complex may be captured on a streptavidin-coated microtiter plate by means of the capture probe, and the chemiluminescent signal is developed and read in a luminometer.

To practice Taqman® real-time PCR, two PCR primers with a preferred product size of 50-150 base pairs are used to amplify the target region. A fluorogenic probe is used for detection of the amplified DNA fragment. The probe is a single stranded oligonucleotide of 19-28 nucleotides in which a reporter dye (e.g., 6-carboxyfluorescein (FAM) or tetrachlorofluorescin (TET)) and a quencher dye tetramethylrhodamine (TAMRA) are attached to the probe. When the reporter dye is separated from the quencher dye, the reporter dye emits energy which is detectable. The probe is designed to bind preferentially to the DNA sequence between the two PCR primers (i.e. the template region extended by polymerase). Thermal cycling causes the primers and probes to anneal and denature producing multiple amplicons. Suitable fluorescent reporters and fluorophores are well known and not described in detail herein. Taqman® real-time PCR takes advantage of the 5'-exonuclease activity of certain polymerase enzymes (e.g. Taq or Tth). During the combined annealing/extension step, the probe hybridizes to the target and 5'→3' exonuclease activity of the polymerase enzyme cleaves the reporter dye. When the reporter dye is separated from the quencher dye, the reporter dye emits energy which is detectable. The resulting fluorescence signal is proportional to the amount of amplified product in the sample.

Both end-point and real-time PCR require additional reagents for hybridization and amplification of the target gene, including buffers, polymerase and free deoxynucleotide triphosphates. For real-time PCR a device that detects the signal and analyzes the signal data is also required. The reagents and equipment are well known to those skilled in the art and are not discussed in detail herein.

In one embodiment, the oligonucleotide primers and probes are configured to amplify and detect the pmpA gene using Taqman® real-time PCR. Three primer and probe sets, specifically designed for the Taqman® real-time PCR assay, are presented in Table 3 below.

TABLE 3

EXAMPLES OF SPECIFIC OLIGONUCLEOTIDE PRIMERS AND PROBES

| Description | Sequence 5'-3' | ~$T_m$ (° C.) | % GC | Location* | SEQ ID NO: |
|---|---|---|---|---|---|
| Forward Primer A | TGG CTC CCA ACA GGA GAA TAT | 57.2 | 48 | 1966-1986 | SEQ ID NO: 10 |
| Reverse Primer A | AAA TGT GCT CCA TAA GGA ATT AGG | 56.6 | 38 | 2020-2043 | SEQ ID NO: 11 |
| Probe A | ACG GCA CGC CCC ACT CGA T | 66.8 | 68 | 2000-2018 | SEQ ID NO: 12 |
| Forward Primer B | CAA CAG GAG AAT ATG TCC TTG AAT C | 57.0 | 40 | 1973-1997 | SEQ ID NO: 13 |
| Reverse Primer B-1 | TCG CTT AAG TTA TGA GAG GCT GTC | 58.0 | 46 | 2055-2078 | SEQ ID NO: 14 |

TABLE 3-continued

EXAMPLES OF SPECIFIC OLIGONUCLEOTIDE PRIMERS AND PROBES

| Description | Sequence 5'-3' | ~$T_m$ (° C.) | % GC | Location* | SEQ ID NO: |
|---|---|---|---|---|---|
| Probe B | TGC CGT TCC TAA TTC CTT ATG GAG CAC A | 68.5 | 46 | 2013-2040 | SEQ ID NO: 15 |
| Reverse Primer B-2 | TAA GTT ATG AGA GGC TGT CTG TAA AAG TA | 56.6 | 34 | 2045-2073 | SEQ ID NO: 16 |

*Genbank Accession AY884095

Specifically, the Forward Primer A oligonucleotide (TGGCTCCCAACAGGAGAATAT; SEQ ID NO:10) described above may hybridize to a complementary target sequence contained within the pmpA gene. More specifically, Forward Primer A binds to the location at about 1966-1986 base pairs of the pmpA gene. This oligonucleotide sequence was specifically designed to bind to this particular region of the pmpA gene. As noted below, and is true with regard to the oligonucleotide primers and probes, the illustrative SEQ ID Numbers are for one hundred percent complementarity with the target binding sequence.

Oligonucleotide primers and probes that are at least 70 percent complementary with the target binding sequence are contemplated.

The Reverse Primer A oligonucleotide (AAATGTGCTCCATAAGGAATTAGG; SEQ ID NO:11) may hybridize to a complementary target sequence contained within the pmpA gene. More specifically, Reverse Primer A binds to the location at about 2020-2043 base pairs of the pmpA gene. This oligonucleotide region sequence was specifically designed to bind to this particular region of the pmpA gene.

The oligonucleotide Probe A has a target binding sequence of (ACGGCACGCCCCACTCGAT; SEQ ID No:12) that specifically binds to base pairs 2000-2018 of the pmpA gene. Many donor/quencher dye pairs known in the art are useful for the detection of amplified genes. These include, but not limited to, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-Docket hydroxysuccinimidyl 1-pyrenesulfonate (PYS)/FITC, FITC/Rhodamine X, FITC/tetramethylrhodamine (TAMRA), 6-Carboxyfluorescein (6-FAM)/TAMRA and others known to those skilled in the art. The selection of a particular donor/quencher pair is not critical. For energy transfer quenching mechanisms it is necessary that the emission wavelengths of the donor fluorophore overlap the excitation wavelengths of the quencher, i.e., there must be sufficient spectral overlap between the two dyes to allow efficient energy transfer, charge transfer or fluorescence quenching. P-(dimethyl aminophenylazo) benzoic acid (DABCYL) is a non-fluorescent quencher dye which effectively quenches fluorescence from an adjacent fluorophore, e.g., fluorescein or 5-(2'-aminoethyl) aminonaphthalene (EDANS). Any dye pair which produces fluorescence quenching in the detection probe of the invention can be used in the methods described herein, regardless of the mechanism by which quenching occurs.

The Forward Primer B oligonucleotide (CAACAGGAGAATATGTCCTTGAATC; SEQ ID NO:13) may hybridize to a complementary target sequence contained within the pmpA gene. More specifically, Forward Primer B binds to the location at about 1973-1997 base pairs of the pmpA gene. This oligonucleotide sequence was designed to bind this particular region of the pmpA gene.

The Reverse Primer B-1 oligonucleotide (TCGCTTAAGTTATGAGAGGCTGTC; SEQ ID NO:14) may hybridize to a complementary target sequence contained within the pmpA gene. More specifically, the Reverse Primer B-1 binds to the location at about 2055-2078 base pairs of the pmpA gene. This oligonucleotide region sequence was specifically designed to bind to this particular region of the pmpA gene.

The oligonucleotide Probe B (TGCCGTTCCTAATTCCTTATGGAG CACA; SEQ ID No:15) was designed to specifically bind to base pairs 2013-2040 of the pmpA gene. Many donor/quencher dye pairs known in the art and described above are useful in the present invention.

An alternate reverse primer design, the Reverse Primer B-2 oligonucleotide, (TAAGTTATGAGAGGCTGTCTGTAAAAG TA; SEQ ID NO:16) may hybridize to a complementary target sequence contained within the pmpA gene. More specifically, Reverse Primer B-2 binds to the location at about 2045-2073 base pairs of the pmpA gene. This oligonucleotide region sequence was specifically designed to bind to this particular region of the pmpA gene The oligonucleotides described above are described in terms of being close to, if not exactly, 100% complementary to their target binding sequences. However, primers and probes can bind to target sequences even though they are less than 100% complementary with those regions. The requisite degree of complementarity depends on a variety of factors including the stringency of the binding conditions. Depending upon the stringency conditions employed, the primers and probes may be modified to include different bases in their sequence and still be sufficiently complementary to bind to the target region of the pmpA nucleic acid. Sufficiently complementary, as used herein, includes complementarity of about 70% or more (e.g. about 72% or more, about 74% or more, about 76% or more, about 78% or more, and so on up to 100%). In preferred embodiments, the complementarity of the primers/probes to their target sequence is at least about 80% or more (e.g. about 82% or more, about 84% or more, about 86% or more, about 88% or more, and so on up to 100%) over the length of the binding portion of the primers/probes. More preferably, the complementarity of the primers and probes to their target sequences is about 90% or more (e.g. about 92% or more, about 94% or more, about 96% or more, about 98% or more, and so on up to 100%).

While the oligonucleotides described herein must be sufficiently complementary to bind their respective portions of the pmpA nucleic acid, it is recognized at some point the sequence of the oligonucleotide becomes less complementary to the sequence in the pmpA nucleic acid and may bind other nucleic acid sequences. Therefore, it is desirable that the oligonucleotide probes remain sufficiently complementary with its respective portion of the pmpA gene, and not lose selectivity for its respective target binding site.

In one embodiment, the oligonucleotide primers and probes described in Table 3 are can be used as three different PCR assay sets. In this embodiment, Assay A refers to an oligonucleotide set comprising pmpA Forward primer A, pmpA Reverse primer A, and pmpA Probe A; Assay B-1 refers to an oligonucleotide set comprising pmpA Forward primer B, pmpA Reverse primer B-1, and pmpA Probe B; and Assay B-2 refers to an oligonucleotide set comprising pmpA Forward primer B, pmpA Reverse primer B-2, and pmpA Probe B. In the context of PCR, the oligonucleotide sets as described may amplify a 78, 106, or 101 base pair portion of the pmpA gene, for oligonucleotide Assay A, oligonucleotide Assay B-1, or oligonucleotide Assay B-2 respectively.

The oligonucleotides as described may also be useful in other amplification assays with or without modification. One of ordinary skill in the art would be capable of adapting the oligonucleotide sequences or portions of the oligonucleotide sequences as described herein for other amplification assays. For example, the oligonucleotide described herein may be useful in Strand Displacement Amplification (SDA), Transcription Mediated Amplification (TMA) and Ligase Chain Reaction (LCR) amplification assays with or without modification.

In one embodiment, the oligonucleotides of this invention are used in a method for detecting and diagnosing whether a biological sample contains C. trachomatis using PCR. In another embodiment, the oligonucleotides are used in a method to amplify a target sequence of the pmpA gene of C. trachomatis and detect C. trachomatis in a biological sample. In yet another embodiment, the method utilizes the Taqman® real-time PCR method for detection of C. trachomatis in a biological sample. In one embodiment, the biological sample is either a blood sample, a urine sample, or a vaginal swab sample.

For commercial convenience, oligonucleotides useful for specific detection and identification of C. trachomatis pmpA nucleic acids may be packaged in the form of a kit. Typically, such a kit contains at least one oligonucleotide described herein. Reagents for performing a nucleic acid amplification reaction may also be included with the C. trachomatis pmpA-specific oligonucleotides. For example, buffers, other oligonucleotides, nucleotide triphosphates, enzymes, etc., may be included. The components of the kit may be packaged together in a common container. Optionally instructions may be included that illustrate one described embodiment for performing a specific embodiment of the inventive methods. Other optional components may also be included in the kit, e.g., an oligonucleotide tagged with a label suitable for use as an assay probe, and/or reagents or means for detecting the label.

In one embodiment a kit may include at least one oligonucleotide useful in the context of PCR. Oligonucleotides described herein may be useful as amplification primers or probes.

In another embodiment, the kit may include at least one oligonucleotide described herein and optional components useful in the context of Taqman® real-time PCR. Such optional components may be buffers, nucleotide triphosphates, enzymes, etc. Optionally, reagents for simultaneously detecting a target sequence, such as a probe, may be included in the kit. One skilled in the art would understand how to optimize such a kit for amplification reactions to detect and identify C. trachomatis utilizing the oligonucleotides described herein.

In yet another embodiment, the kit may be used to detect and diagnose whether a clinical sample contains C. trachomatis pmpA DNA. The clinical sample may be added to the kit so that a nucleic acid sequence may be amplified and detected using the oligonucleotides described herein.

Furthermore, the kit may include oligonucleotides and reagents for Taqman® real-time PCR in dried or liquid format. The components of the kit may be more stable and easily manipulated when in dried format. The dried components of the kit may be added or pre-treated to a solid phase such as microtiter plate, microarray, or other appropriate receptacle, where the sample and PCR buffer need only be added. This format facilitates assaying multiple samples simultaneously and is useful in high throughput methods. The BD MAX™, BD Viper™ LT and Viper™ HT instruments may be used. All are trademarks of Becton Dickinson and Co.

EXAMPLES

Example 1

C. trachomatis Target Region Positive Control

A 342 base pair DNA fragment that is 100% identical to nucleotides 1835-2176 of the pmpA gene from C. trachomatis serovar H, strain UW-4 was synthesized de novo. The fragment was ligated into the vector Blue Heron Bio pUC (Blue Heron Biotechnology) and the recombinant plasmid, CTpmpA, was transformed into SC110 competent cells (Stratagene catalog number 200247). Plasmid DNA was purified from the SCS110 competent cells through a cesium chloride gradient and linearized by digestion with EcoR1 enzyme (Roche catalog number 10200310001). The purified plasmid DNA was quantified by UV spectrophotometry. The resulting DNA fragment was used as a positive control in several of the following Examples.

Example 2

Functional Performance of pmpA Assay A

Various amounts of the CTpmpA plasmid were used to test the functionality of the pmpA Assay A. The range of concentrations of the CTpmpA plasmid included $1 \times 10^6$, $1 \times 10^5$, $1 \times 10^4$, $1 \times 10^3$, 100, and 10 copies per reaction. Four replicates were tested at each target concentration, as well as four no-template replicates as a negative control. For each replicate, CTpmpA recombinant plasmid containing C. trachomatis target DNA was diluted in 5 mM Tris pH 8.0. The diluted plasmid was then added to the wells of a 96-well microtiter plate containing TaqMan® Universal PCR Master Mix (Applied Biosystems catalog number 43021437), 900.0 nM pmpA FwdA (SEQ. ID NO. 10), 900.0 nM pmpA RevA (SEQ ID NO. 11), and 250.0 nM pmpA ProbeA (SEQ ID NO. 12). Real-time PCR amplification and detection was performed using the ABI 7500 sequence detection system (Applied Biosystems). The thermal cycling profile was: Cycle 1 at 50° C. for 2 minutes followed by 95° C. for 10 minutes; Cycles 2-46 at 95° C. for 15 seconds followed by 59° C. for 1 minute.

Results were obtained by absolute quantification using the Delta Rn analysis method known to those skilled in the art and not described in detail herein. Positive results were obtained from all replicates (4/4) at each of $1 \times 10^6$, $1 \times 10^5$, $1 \times 10^4$, $1 \times 10^3$, 100, and 10 copies per reaction. Negative results were obtained from all (4/4) no-template control replicates. The results were analyzed by linear regression to calculate the efficiency of the PCR reaction. The slope of the standard curve was −3.39 and the percent efficiency of the reaction was 97.0%. The results indicate the CTpmpA plasmid works well as a positive control for real-time PCR assays that amplify and detect the target region of the pmpA gene (SEQ ID NO. 2—base pairs 1835-2176) using the oligonucleotides of pmpA Assay A. In addition, the results indicate that the oligonucleotides of pmpA Assay A directed towards the target region of the pmpA gene (SEQ ID NO. 2-bases 1835-2176) can accurately amplify and detect the pmpA gene in a TaqMan® real-time PCR system.

Example 3

Functional Performance of pmpA Assay B

Various amounts of the CTpmpA plasmid were used to test the functionality of the pmpA Assay B. The range of concentrations of CTpmpA plasmid included 1×10$^6$, 1×10$^5$, 1×10$^4$, 1×10$^3$, 100, and 10 copies per reaction. Four replicates were tested at each target concentration, as well as four no-template replicates as a negative control. For each replicate, CTpmpA recombinant plasmid containing *C. trachomatis* target DNA was diluted in 5 mM Tris pH 8.0. The diluted plasmid was then added to the wells of a 96-well multi-well microtiter plate containing TaqMan® Universal PCR Master Mix (Applied Biosystems catalog number 4304437), 900.0 nM pmpA FwdB (SEQ. ID NO. 13), 900.0 nM pmpA RevB-2 (SEQ ID NO. 16), and 250.0 nM pmpA ProbeB (SEQ ID NO. 15). Real-time PCR amplification and detection was performed using the ABI 7500 sequence detection system (Applied Biosystems). The thermal cycling profile was: Cycle 1 at 50° C. for 2 minutes followed by 95° C. for 10 minutes; Cycles 2-46 at 95° C. for 15 seconds followed by 59° C. for 1 minute.

Results were obtained by absolute quantification using the Delta Rn analysis method. Positive results were obtained from all replicates (4/4) at each of 1×10$^6$, 1×10$^5$, 1×10$^4$, 1×10$^3$, 100, and 10 copies per reaction. Negative results were obtained from all (4/4) no-template control replicates. The results were analyzed by linear regression to calculate the efficiency of the PCR reaction. The slope of the standard curve was −3.49 and the percent efficiency of the reaction was 93.4%. The results indicate the CTpmpA plasmid works well as a positive control for real-time PCR assays that amplify and detect the target region of the pmpA gene (SEQ ID NO. 2—base pairs 1835-2176) using the oligonucleotides of pmpA Assay B. In addition, the results indicate that the oligonucleotides of pmpA Assay B directed toward the target region of the pmpA gene (SEQ ID NO. 2—base pairs 1835-2176) can accurately amplify and detect the pmpA gene in a real-time PCR system.

Example 4

Specificity Testing

Specificity testing was performed with three replicates each of seventy-six (76) different organisms found in normal and abnormal vaginal flora. *C. trachomatis* serovar H genomic DNA (ATCC catalog number VR-879D) at 100 copies per reaction was used as a positive control. Each organism was diluted in 10 mM Tris pH 8.0 to deliver 1×10$^4$ copies per 10 μL of the total real-time PCR reaction buffer. Each of the diluted samples were added to wells of a 96-well microtiter plate containing reaction buffer. The final composition of the reaction buffer is summarized in Table 4 below.

TABLE 4

Final PCR Reaction Conditions

| Component | Final Concentration |
|---|---|
| Tris pH 8.0 | 70 mM |
| NaOH | 5.0 mM |
| CTpmpA Fwd A | 0.60 μM |
| CTpmpA Rev A | 0.60 μM |
| CTpmpA Probe A, FAM/Black Hole Quencher 1 | 0.40 μM |
| MgCl$_2$ | 3.5 mM |
| dATP | 0.05 mM |
| dCTP | 0.05 mM |
| dGTP | 0.05 mM |
| dTTP | 0.05 mM |
| Taq polymerase | 2.7 Units |

Real-time PCR was performed using the CFX96™ Real-Time PCR System (Bio-Rad Laboratories Inc.). The thermal cycling profile was: Cycle 1 at 95° C. for 15 minutes; Cycles 2-51 at 95° C. for 15 seconds followed by 60° C. for 1 minute.

The amplification assay in this example was performed in a multiplex format, i.e., multiple genes were amplified and detected in a single assay for the identification of multiple organisms in a sample. In this example reagents for the amplification and detection of two additional targets were combined with the reagents used for the amplification and detection of the pmpA gene of *C. trachomatis*. One of the additional genes, referred to as Multiplex Assay B, is used to amplify and detect the presence of *Neisseria gonorrhea* in a sample. The second additional gene, referred to as Multiplex Assay C, is used to amplify and detect the presence of *Trichomonas vaginalis* in a sample.

The results were obtained by the Delta Rn analysis and are summarized in Table 5 below. The results indicate that oligonucleotides directed towards the target region of the pmpA gene (SEQ ID NO. 2—bases 1835-2176) did not cross-react with other microorganisms that may be found in a clinical sample and are specific for *C. trachomatis*. In addition, the data demonstrates that the oligonucleotides described herein that amplify and detect the pmpA gene of *C. trachomatis* can be used in a multiplex system. Not only is a detectable signal obtained for the pmpA gene, but a detectable signal can be obtained for the additional target genes as well. This indicates that the reagents and oligonucleotides used in the pmpA assay do not interfere with the reagents used for the amplification and detection of additional gene targets.

TABLE 5

Specificity Test Results

| Organism | pmpA Assay | Multiplex Assay B | Multiplex Assay C |
|---|---|---|---|
| *Neisseria gonorrhea* | Negative | Positive | Negative |
| *Trichomonas vaginalis* | Negative | Negative | Positive |
| *Cryptococcus neoformans* | Negative | Negative | Negative |
| *Enterococcus faecalis* | Negative | Negative | Negative |
| *Enterococcus faecium* | Negative | Negative | Negative |
| *Klebsiella ozaeneae* | Negative | Negative | Negative |
| *Proteus mirabilis* | Negative | Negative | Negative |
| *Salmonella cholerasuis* | Negative | Negative | Negative |
| *Salmonella typhimurium* | Negative | Negative | Negative |
| *Staphylococcus aureus*, non-protein A | Negative | Negative | Negative |
| *Staphylococcus aureus*, protein-A producing | Negative | Negative | Negative |
| *Staphylococcus epidermidis* | Negative | Negative | Negative |
| *Streptococcus pyogenes* (Group A) | Negative | Negative | Negative |

TABLE 5-continued

Specificity Test Results

| Organism | pmpA Assay | Multiplex Assay B | Multiplex Assay C |
|---|---|---|---|
| Streptococcus mitis | Negative | Negative | Negative |
| Streptococcus mitis | Negative | Negative | Negative |
| Streptococcus mutans | Negative | Negative | Negative |
| Streptococcus pneumoniae | Negative | Negative | Negative |
| Streptomyces griseus | Negative | Negative | Negative |
| Vibrio parahaemolyticus | Negative | Negative | Negative |
| Yersinia enterocolitica | Negative | Negative | Negative |
| Acinetobacter calcoaceticus | Negative | Negative | Negative |
| Acinetobacter lwoffi | Negative | Negative | Negative |
| Aeromonas hydrophilia | Negative | Negative | Negative |
| Alcaligenes faecalis | Negative | Negative | Negative |
| Bacillus subtilis | Negative | Negative | Negative |
| Candida albicans | Negative | Negative | Negative |
| Candida glabrata | Negative | Negative | Negative |
| Candida tropicalis | Negative | Negative | Negative |
| Citrobacter freundii | Negative | Negative | Negative |
| Corynebacterium renale | Negative | Negative | Negative |
| Edwardsiella tarda | Negative | Negative | Negative |
| Enterobacter cloacae | Negative | Negative | Negative |
| Flavobacterium meningosepticum | Negative | Negative | Negative |
| Gemella haemolysans | Negative | Negative | Negative |
| Haemophilus influenzae | Negative | Negative | Negative |
| Kingella kingae | Negative | Negative | Negative |
| Lactobacillus jensenii | Negative | Negative | Negative |
| Moraxella osloensis | Negative | Negative | Negative |
| Moraxella osloensis | Negative | Negative | Negative |
| Morganella morganii | Negative | Negative | Negative |
| Plesiomonas shigelloides | Negative | Negative | Negative |
| Providencia stuartii | Negative | Negative | Negative |
| Rhodococcus equi | Negative | Negative | Negative |
| Salmonella minnesota | Negative | Negative | Negative |
| Streptcoccus bovis | Negative | Negative | Negative |
| Corynebacterium xerosis | Negative | Negative | Negative |
| Peptostreptococcus anaerobius | Negative | Negative | Negative |
| E coli transfected with HPV 6 DNA | Negative | Negative | Negative |
| E coli transfected with HPV 11 DNA | Negative | Negative | Negative |
| E coli transfected with HPV 16 DNA | Negative | Negative | Negative |
| E coli transfected with HPV 18 DNA | Negative | Negative | Negative |
| Veillonella parvula | Negative | Negative | Negative |
| Clostridium perfringens | Negative | Negative | Negative |
| Lactobacillus acidophilus | Negative | Negative | Negative |
| Bacteroides fragilis | Negative | Negative | Negative |
| Peptostreptococcus anaerobius | Negative | Negative | Negative |
| Pseudomonas aeruginosa | Negative | Negative | Negative |
| Peptostreptococcus productus | Negative | Negative | Negative |
| Propionibacterium acnes | Negative | Negative | Negative |
| Pseudomonas fluorescens | Negative | Negative | Negative |
| Pseudomonas putida | Negative | Negative | Negative |
| Candida parapsilosis | Negative | Negative | Negative |
| Legionella pneumophilia | Negative | Negative | Negative |
| Mycobacterium smegmatis | Negative | Negative | Negative |
| Campylobacter jejuni | Negative | Negative | Negative |
| Mobiluncus mulieris | Negative | Negative | Negative |
| Actinomyces israelii | Negative | Negative | Negative |
| Lactobacillus brevis | Negative | Negative | Negative |
| Bifidobacterium adolescentis | Negative | Negative | Negative |
| Clostridium difficile | Negative | Negative | Negative |
| Atopobium vaginae | Negative | Negative | Negative |
| Anaerococcus vaginalis | Negative | Negative | Negative |
| Bifidobacterium infantis | Negative | Negative | Negative |
| Bifidobacterium brevis | Negative | Negative | Negative |
| Micrococcus leutus | Negative | Negative | Negative |
| Leuconostoc paramensenteroides | Negative | Negative | Negative |
| Lactobacillus vaginalis | Negative | Negative | Negative |
| C. trachomatis serovar H genomic DNA (Positive control) | Positive | Negative | Negative |

Example 5

Lysis of C. trachomatis Organism and Quantitation by Real-Time PCR

A stock of C. trachomatis was diluted 1:10 in 16.7 mM Tris pH 8.0 and 1.12% Tween®-20. The diluted stock was then added to wells of a 96-well microtiter plate containing 1× reaction master mix consisting of 15 mM Tris pH 8.0, 50 mM KCl, 0.01% Tween®-20, 3.0 mM $MgCl_2$, 0.20 mM dATP, 0.20 mM dCTP, 0.20 mM dGTP, 0.20 mM dTTP, 120.0 nM ROX passive reference dye, 600 nM pmpA FwdA, 600 nM pmpA RevA, and 400 nM pmpA Probe A. The concentration of Tween®-20 in the final reaction mixture was 0.2%.

To prepare a standard curve, the CTpmpA recombinant plasmid containing C. trachomatis target DNA was diluted in a mixture of 15 mM Tris pH 8.0 and 1% Tween®-20 at $1 \times 10^6$, $1 \times 10^5$, $1 \times 10^4$, $1 \times 10^3$, 100, and 10 copies per reaction. The diluted plasmid was then added to microwells containing the same 1× master mix used for the stock of C. trachomatis.

Real-time PCR was performed using the ABI 7500 sequence detection system (Applied Biosystems). The thermal cycling profile was: Cycle 1 at 95° C. for 15 minutes; Cycles 2-46 at 95° C. for 15 seconds followed by 59° C. for 1 min.

Results were obtained by absolute quantification using the Delta Rn analysis method. Lysis of the organism occurred in the presence of 0.2% Tween®-20 during cycle 1. The results of the standard curve were analyzed by linear regression to calculate the efficiency of the PCR reaction. The slope of the standard curve was −3.35 and the percent efficiency of the reaction was 98.9%. The R-squared result was 0.998. The standard curve was used to determine by absolute quantitation that the concentration of C. trachomatis in the original stock solution was $1.10 \times 10^6$ EB/ml. The results indicate that extraction buffers containing a non-ionic detergent, for example Tween®-20, can be added to the real-time PCR reaction buffer in order to sufficiently lyse the microbial cells and extract the DNA prior to amplification of the target gene. Additionally, the extraction reagents do not interfere with the amplification reaction reagents and therefore do not require additional clean-up steps to remove the extraction buffer detergents prior to amplification. This allows for the accurate quantitation of the pmpA gene in a sample.

Example 6

Sensitivity Testing of CTpmpA Assay

A Twelve replicates each of 250, 125, 70, 35, 15, 5, and 1.5 elementary bodies (EBs) per reaction of C. trachomatis serovar H were diluted in 10 mM Tris pH 8.0 at and analyzed by real-time PCR using the oligonucleotides of the pmpA Assay A. Twelve replicates of no-template control (NTC) reactions were included in the assay as a negative control. Each of the samples were added to wells of a 96-well microtiter plate containing reaction buffer. The composition of the final reaction buffer is summarized in Table 6 below.

NO. 2—base pairs 1835-2176) allow for the amplification and detection of the pmpA gene across a wide range of concentration including very dilute samples.

TABLE 7 pmpA Assay A Sensitivity Test Results

| | C. trachomatis Serovar H Concentration (EB per reaction) | | | | | | | |
|---|---|---|---|---|---|---|---|---|
| | 250 | 125 | 70 | 35 | 15 | 5 | 1.5 | NTC |
| Ct | 28.87 | 30.85 | 30.95 | 31.92 | 32.82 | 34.70 | 36.04 | Negative |
| | 29.24 | 30.92 | 30.89 | 31.93 | 33.09 | 34.41 | 37.98 | Negative |
| | 28.68 | 30.11 | 30.75 | 31.59 | 32.68 | 35.71 | 37.18 | Negative |
| | 29.21 | 31.02 | 31.44 | 32.22 | 34.46 | 36.15 | 36.24 | Negative |
| | 29.34 | 30.70 | 30.55 | 31.87 | 32.81 | 34.17 | 35.19 | Negative |
| | 28.94 | 30.76 | 30.92 | 32.49 | 32.62 | 34.83 | 35.62 | Negative |
| | 29.2 | 31.10 | 31.13 | 32.16 | 32.51 | 36.42 | 36.27 | Negative |
| | 29.08 | 30.32 | 30.85 | 31.99 | 32.74 | 35.09 | 35.88 | Negative |
| | 29.3 | 31.26 | 30.61 | 32.71 | 32.98 | 34.98 | 36.34 | Negative |
| | 29.21 | 30.50 | 31.34 | 32.21 | 34.15 | 34.64 | 36.56 | Negative |
| | 29.3 | 30.90 | 30.58 | 32.23 | 33.31 | 36.03 | 35.11 | Negative |
| | 29.41 | 30.89 | 31.17 | 32.19 | 33.51 | 34.51 | 37.07 | Negative |
| Ct Mean | 29.25 | 30.83 | 30.95 | 32.25 | 33.20 | 35.28 | 36.20 | N/A |
| StDev | 0.11 | 0.36 | 0.32 | 0.24 | 0.59 | 0.77 | 0.66 | N/A |
| CV | 0.39% | 1.15% | 1.02% | 0.75% | 1.77% | 2.19% | 1.83% | N/A |

TABLE 6

Final PCR reaction conditions

| Component | Final Concentration |
|---|---|
| Tris pH 8.0 | 70 mM |
| NaOH | 5.0 mM |
| CTpmpA Fwd A | 0.60 μM |
| CTpmpA Rev A | 0.60 μM |
| CTpmpA Probe A FAM/ Black Hole Quencher 1 | 0.40 μM |
| MgCl$_2$ | 3.5 mM |
| dATP | 0.05 mM |
| dCTP | 0.05 mM |
| dGTP | 0.05 mM |
| dTTP | 0.05 mM |
| Taq polymerase | 2.7 Units |
| Trehalose | 6% |
| ROX | 120.00 nM |

Real-time PCR was performed using the ABI 7500 sequence detection system (Life Technologies) with a passive reference dye. The thermal cycling profile was: Cycle 1 at 95° C. for 15 minutes; Cycles 2-51 at 95° C. for 15 seconds followed by 60° C. for 1 minute.

The results were obtained by Delta Rn analysis method and are summarized in Table 7 below. Cycle threshold (Ct) is the cycle number in which there is sufficient amplified product to yield a detectable fluorescent signal. A Ct of less than or equal to 40 indicates a positive sample. In this example, the low standard deviation (StDev) demonstrates that the individual data points are very close to the mean and there is very little variability in the data, demonstrating reproducibility of the assay. In this table, the coefficient of variation (CV) is the relative standard deviation, expressed as a percentage. As Table 7 indicates, the oligonucleotides of CTpmpA Assay A demonstrated 100% sensitivity across the range of concentrations, including the lowest concentration of 1.5 EB per reaction. All no-template control (NTC) reactions were negative, as expected. These results indicate that oligonucleotides directed towards the target region of the pmpA gene (SEQ ID Example 7

Ubiquity Testing

Ubiquity testing was performed across a panel of fifteen different serovars of C. trachomatis with the pmpA Assay A oligonucleotides. C. trachomatis serovar H genomic DNA (ATCC VR-879D) was tested as a positive control. Four replicates of each of the serovars at 100 EBs per reaction were diluted in 10 mM Tris pH 8. Each of the samples was added to wells of a 96-well microtiter plate containing reaction buffer. The composition of the final reaction buffer is summarized in Table 8 below.

TABLE 8

Final PCR Reaction Conditions

| Component | Final Concentration |
|---|---|
| Tris pH 8.0 | 70 mM |
| NaOH | 5.0 mM |
| pmpA Fwd A | 0.60 μM |
| pmpA Rev A | 0.60 μM |
| pmpA FAM Probe A FAM/ Black Hole Quencher 1 | 0.40 μM |
| MgCl$_2$ | 3.5 mM |
| dATP | 0.05 mM |
| dCTP | 0.05 mM |
| dGTP | 0.05 mM |
| dTTP | 0.05 mM |
| Taq polymerase | 2.7 Units |

Real-time PCR was performed using the Mx3005P QPCR system (Stratagene). The thermal cycling profile was: Cycle 1 at 95° C. for 15 minutes; Cycles 2-51 at 95° C. for 15 seconds followed by 60° C. for 1 minute.

The results were obtained by the Delta Rn analysis method and are summarized in Table 9 below.

TABLE 9

Ubiquity Test Results

| Organism | ID | Test Result |
| --- | --- | --- |
| C. trachomatis Serovar A | ATCC VR-571B | Positive |
| C. trachomatis Serovar B | ATCC VR-573 | Positive |
| C. trachomatis Serovar Ba | ATCC VR-347 | Positive |
| C. trachomatis Serovar C | ATCC VR-572 | Positive |
| C. trachomatis Serovar D | ATCC VR-885 | Positive |
| C. trachomatis Serovar E | ATCC VR-248B | Positive |
| C. trachomatis Serovar F | ATCC VR-346 | Positive |
| C. trachomatis Serovar G | ATCC VR-878 | Positive |
| C. trachomatis Serovar I | ATCC VR-880 | Positive |
| C. trachomatis Serovar J | ATCC VR-886 | Positive |
| C. trachomatis Serovar K | ATCC VR-887 | Positive |
| C. trachomatis Serovar LGV1 | ATCC VR-901B | Positive |
| C. trachomatis Serovar LGV2 | ATCC VR-902B | Positive |
| C. trachomatis Serovar LGV3 | ATCC VR-903 | Positive |
| C. trachomatis genomic DNA | ATCC VR-879D | Positive |

The results demonstrate that all fifteen of the *C. trachomatis* serovars, including the positive control for serovar H, are detectable using oligonucleotides directed towards the target region of the pmpA gene (SEQ ID NO. 2—base pairs 1835-2176).

Example 8

Detection of *C. trachomatis* Variant E

A viable culture of *C. trachomatis* variant E was obtained and propagated in vitro. (Statens Serum Institute) Four replicates of the *C. trachomatis* variant E were diluted to a final concentration of 10 EB per reaction in sample preparation buffer. The composition of the sample preparation buffer is summarized in Table 10 below. Four replicates of *C. trachomatis* wild type serovar E and *C. trachomatis* serovar H at 10 EB per reaction were used as positive controls.

TABLE 10

| Sample Preparation Buffer Formulation | |
|---|---|
| Component | Final Concentration |
| Tris pH 8.0 | 100 mM |
| $MgCl_2$ | 5.0 mM |
| NaOH | 10.0 mM |
| Proclin 300 | 0.02% |
| Tween ®-20 | 0.01% |

Real-time PCR was performed using the CFX96™ Real-Time PCR System (Bio-Rad Laboratories Inc.). The thermal cycling profile was: Cycle 1 at 95° C. for 15 minutes; Cycles 2-51 at 95° C. for 15 seconds followed by 60° C. for 1 minute. Each of the samples were added to wells of a 96-well microtiter plate containing reaction mix buffer. The composition of the final reaction buffer is summarized in Table 11 below.

TABLE 11

| Final PCR Reaction Conditions | |
|---|---|
| Component | Final Concentration |
| Tris pH 8.0 | 80 mM |
| NaOH | 8.0 mM |
| pmpA Fwd A | 0.60 μM |
| pmpA Rev A | 0.60 μM |
| pmpA FAM Probe A FAM/ Black Hole Quencher 1 | 0.40 μM |
| $MgCl_2$ | 4.0 mM |
| dATP | 0.05 mM |
| dCTP | 0.05 mM |
| dGTP | 0.05 mM |
| dTTP | 0.05 mM |
| Proclin 300 | 0.015% |
| Tween ®-20 | 0.080% |
| Taq polymerase | 2.7 Units |

The results were obtained by the Delta Rn analysis method and are summarized in Table 12 below. All three *C. trachomatis* serovars, i.e., variant E, wild type E and serovar H, were detected using oligonucleotides directed towards the target region of the pmpA gene (SEQ ID NO. 2—base pairs 1835-2176).

TABLE 12

| Detection of *C. trachomatis* Variant E | | |
|---|---|---|
| Organism | ID | Test Result |
| *C. trachomatis* serovar H | ATCC VR-879 | Positive |
| *C. trachomatis* serovar E, wild type | ATCC VR 248B | Positive |
| *C. trachomatis* serovar E, variant | Statens Serum Institute | Positive |

Although the invention herein has been described with reference to particular embodiments, it is to be understood that these embodiments are merely illustrative of the principles and applications of the invention described herein. It is therefore to be understood that numerous modifications may be made to the illustrative embodiments and that other arrangements may be devised without departing from the spirit and scope of the invention described herein as defined by the appended claims.

The invention claimed is:

1. A method for detecting *Chlamydia trachomatis* in a biological sample comprising:
   providing a biological sample;
   contacting the biological sample with a substance comprising an oligonucleotide set that comprises at least one oligonucleotide probe that is detectably labeled and has a nucleotide sequence length of about 10 to about 50 and at least two oligonucleotide primers each having a nucleotide sequence length of about 10 to about 150, under conditions such that the probes and primers anneal to SEQ ID NO:2 at the location between about base pairs 1835-2176 of the pmpA gene;
   wherein the probe comprises a sequence selected from the group consisting of SEQ ID NO:12, SEQ ID NO:15 and oligonucleotide sequences that are at least 70% homologous to SEQ ID NO:12, and SEQ ID NO:15 and the primers comprise oligonucleotide sequences selected from the group consisting of SEQ ID NO:10, SEQ ID NO:11, SEQ ID NO:13, SEQ ID NO:14, SEQ ID NO:16 and oligonucleotide sequences that are at least 70% homologous to SEQ ID NO:10, SEQ ID NO:11, SEQ ID NO:13, SEQ ID NO:14 and SEQ ID NO:16;
   amplifying the target sequence between the two primers using polymerase chain reaction; and
   detecting the label as an indication of the hybridization of the probe set to the target sequence thereby indicating the presence or amount of *Chlamydia trachomatis* in the biological sample.

2. The method of claim 1 wherein, the oligonucleotide set comprises a probe comprising a sequence selected from the group consisting of SEQ ID NO:12 and SEQ ID NO:15 and oligonucleotide sequences that are at least 80% homologous to SEQ ID NO:12 and SEQ ID NO:15.

3. The method of claim 1, wherein the oligonucleotide set comprises a probe comprising a sequence selected from the group consisting of SEQ ID NO:12, SEQ ID NO:15 and oligonucleotide sequences that are at least 90% homologous to SEQ ID NO:12 and SEQ ID NO:15.

4. The method of claim 1, wherein the oligonucleotide primers comprise at least two primers comprising sequences selected from the group consisting of SEQ ID NO:10, SEQ ID NO:11, SEQ ID NO:13, SEQ ID NO:14, SEQ ID NO:16 and oligonucleotide sequences that are at least 80% homologous to SEQ ID NO:10, SEQ ID NO:11, SEQ ID NO:13, SEQ ID NO:14 and SEQ ID NO:16.

5. The method of claim 1, wherein the oligonucleotide primers comprise at least two primers comprising sequences selected from the group consisting of SEQ ID NO:10, SEQ ID NO:11, SEQ ID NO:13, SEQ ID NO:14, SEQ ID NO:16 and oligonucleotide sequences that are at least 90% homologous to SEQ ID NO:10, SEQ ID NO:11, SEQ ID NO:13, SEQ ID NO:14 and SEQ ID NO:16.

6. The method of claim 1, wherein the oligonucleotide set is selected from the group consisting of a first oligonucleotide set comprising oligonucleotide primers having an oligonucleotide sequence comprising SEQ ID NO:10 and SEQ ID NO:11 and an oligonucleotide probe having an oligonucleotide sequence comprising SEQ ID No:12; a second oligonucleotide set comprising oligonucleotide primers having an oligonucleotide sequence comprising SEQ ID NO:13 and SEQ ID NO:14 and an oligonucleotide probe having an oligonucleotide sequence comprising SEQ ID NO:15; and a third oligonucleotide set comprising oligonucleotide primers having an oligonucleotide sequence comprising SEQ ID NO:13 and SEQ ID NO:16 and an oligonucleotide probe having an oligonucleotide sequence comprising SEQ ID NO:15.

7. The method of claim 1, wherein the oligonucleotide primers are selected from the group consisting of SEQ ID NO:10, SEQ ID NO:11, and oligonucleotide sequences that are at least 70% homologous to SEQ ID NO:10 and SEQ ID NO:11; and the oligonucleotide probe is selected from the group consisting of SEQ ID No:12 and oligonucleotide sequences that are at least 70% homologous to SEQ ID NO:12.

8. The method of claim 7, wherein the oligonucleotide primers consist of SEQ ID NO:10 and SEQ ID NO:11, and the oligonucleotide probe consists of SEQ ID NO:12.

9. The method of claim 1, wherein the probes and primers anneal to SEQ ID NO:2 at the location between about base pairs 1966-2073 of the pmpA gene.

10. The method of claim 1, wherein the detectable label is a fluorescence marker.

11. The method of claim 1, wherein the polymerase chain reaction is real-time polymerase chain reaction.

12. The method of claim 1, wherein the method is performed in a multi-plex platform.

13. An oligonucleotide set for the detection of the pmpA gene of *Chlamydia trachomatis* in a biological sample comprising at least one oligonucleotide probe that is modified by attachment of a detectable label and has a nucleotide sequence length of about 10 to about 50, and at least two oligonucleotide primers, each of which has a nucleotide sequence length of about 10 to about 150,
   wherein the probes and primers target the nucleotides of SEQ ID NO:2 at the location between about base pairs 1835-2176 of the pmpA gene;
   wherein the at least one probe comprises a sequence selected from the group consisting of SEQ ID NO:12, SEQ ID NO:15 and oligonucleotide sequences that are at least 70% homologous to SEQ ID NO:12, and SEQ ID NO:15 and the at least two primers comprise oligonucleotide sequences selected from the group consisting of SEQ ID NO:10, SEQ ID NO:11, SEQ ID NO:13, SEQ ID NO:14, SEQ ID NO:16 and oligonucleotide sequences that are at least 70% homologous to SEQ ID NO:10, SEQ ID NO:11, SEQ ID NO:13, SEQ ID NO:14 and SEQ ID NO:16.

14. The oligonucleotide set of claim 13, wherein the at least one probe comprises a sequence selected from the group consisting of SEQ ID NO:12 and SEQ ID NO:15 and oligonucleotide sequences that are at least 80% homologous to SEQ ID NO:12 and SEQ ID NO:15.

15. The oligonucleotide set of claim 13, wherein the at least one probe comprises a sequence selected from the group consisting of SEQ ID NO:12, SEQ ID NO:15 and oligonucleotide sequences that are at least 90% homologous to SEQ ID NO:12 and SEQ ID NO:15.

16. The oligonucleotide set of claim 13, wherein the at least two primers comprise sequences selected from the group consisting of SEQ ID NO:10, SEQ ID NO:11, SEQ ID NO:13, SEQ ID NO:14, SEQ ID NO:16 and oligonucleotide sequences that are at least 80% homologous to SEQ ID NO:10, SEQ ID NO:11, SEQ ID NO:13, SEQ ID NO:14 and SEQ ID NO:16.

17. The oligonucleotide set of claim 13, wherein the at least two primers comprising sequences selected from the group consisting of SEQ ID NO:10, SEQ ID NO:11, SEQ ID NO:13, SEQ ID NO:14, SEQ ID NO:16 and oligonucleotide sequences that are at least 90% homologous to SEQ ID NO:10, SEQ ID NO:11, SEQ ID NO:13, SEQ ID NO:14 and SEQ ID NO:16.

18. The oligonucleotide set of claim 13, wherein the oligonucleotide set is selected from the group consisting of a first oligonucleotide set comprising oligonucleotide primers having an oligonucleotide sequence comprising SEQ ID NO:10 and SEQ ID NO:11 and an oligonucleotide probe having an oligonucleotide sequence comprising SEQ ID No:12, a second oligonucleotide set comprising oligonucleotide primers having an oligonucleotide sequence comprising SEQ ID NO:13 and SEQ ID NO:14 and an oligonucleotide probe having an oligonucleotide sequence comprising SEQ ID NO:15 and a third oligonucleotide set comprising oligonucleotide primers having an oligonucleotide sequence comprising SEQ ID NO:13 and SEQ ID NO:16 and an oligonucleotide probe having an oligonucleotide sequence comprising SEQ ID NO:15.

19. The oligonucleotide set of claim 18, wherein the oligonucleotide primers consist of SEQ ID NO:10 and SEQ ID NO:11, and the oligonucleotide probe consists of SEQ ID NO:12.

20. The oligonucleotide set of claim 13, wherein the primers and probes target the nucleotides of SEQ ID NO:2 at the location between about base pairs 1966-2073 on the pmpA gene.

21. The oligonucleotide set of claim 13, wherein the detectable label is a fluorescence marker.

22. A kit for the detection of the pmpA gene of *Chlamydia trachomatis* in a biological sample comprising:
at least one oligonucleotide probe that is modified by attachment of a detectable label and has a nucleotide sequence length of about 10 to about 50, and at least two oligonucleotide primers, each of which has a nucleotide sequence length of about 10 to about 150,
wherein the probes and primers target the nucleotides of SEQ ID NO:2 at the location between about base pairs 1835-2176 on the pmpA gene;
wherein the at least one probe comprises a sequence selected from the group consisting of SEQ ID NO:12, SEQ ID NO:15 and oligonucleotide sequences that are at least 70% homologous to SEQ ID NO:12, and SEQ ID NO:15 and the at least two primers comprise oligonucleotide sequences selected from the group consisting of SEQ ID NO:10, SEQ ID NO:11, SEQ ID NO:13, SEQ ID NO:14, SEQ ID NO:16 and oligonucleotide sequences that are at least 70% homologous to SEQ ID NO:10, SEQ ID NO:11, SEQ ID NO:13, SEQ ID NO:14 and SEQ ID NO:16.

23. The kit of claim 22, wherein the at least one probe comprises an oligonucleotide sequence selected from the group consisting of SEQ ID NO:12, SEQ ID NO:15 and oligonucleotide sequences that are at least 80% homologous to SEQ ID NO:12 and SEQ ID NO:15.

24. The kit of claim 22, wherein the at least one probe comprises a oligonucleotide sequence selected from the group consisting of SEQ ID NO:12, SEQ ID NO:15, and oligonucleotide sequences that are at least 90% homologous to SEQ ID NO:12 and SEQ ID NO:15.

25. The kit of claim 22, wherein the at least two primers comprise oligonucleotide sequences selected from the group consisting of SEQ ID NO:10, SEQ ID NO:11, SEQ ID NO:13, SEQ ID NO:14, SEQ ID NO:16, and oligonucleotide sequences that are at least 80% homologous to SEQ ID NO:10, SEQ ID NO:11, SEQ ID NO:13, SEQ ID NO:14, and SEQ ID NO:16.

26. The kit of claim 22, wherein the at least two primers comprise oligonucleotide sequences selected from the group consisting of SEQ ID NO:10, SEQ ID NO:11, SEQ ID NO:13, SEQ ID NO:14, SEQ ID NO:16, and oligonucleotide sequences that are at least 90% homologous to SEQ ID NO:10, SEQ ID NO:11, SEQ ID NO:13, SEQ ID NO:14, and SEQ ID NO:16.

27. The kit of claim 22, wherein the oligonucleotide set is selected from the group consisting of a first oligonucleotide set comprising oligonucleotide primers having an oligonucleotide sequence comprising SEQ ID NO:10 and SEQ ID NO:11 and an oligonucleotide probe having an oligonucleotide sequence comprising SEQ ID NO:12, a second oligonucleotide set comprising oligonucleotide primers having an oligonucleotide sequence comprising SEQ ID NO:13 and SEQ ID NO:14 and an oligonucleotide probe having an oligonucleotide sequence comprising SEQ ID NO:15 and a third oligonucleotide set comprising oligonucleotide primers having an oligonucleotide sequence comprising SEQ ID NO:13 and SEQ ID NO:16 and an oligonucleotide probe having an oligonucleotide sequence comprising SEQ ID NO:15.

28. The kit of claim 22, wherein the at least two primers are selected from the group consisting of SEQ ID NO:10, SEQ ID NO:11, and oligonucleotide sequences that are at least 70% homologous to SEQ ID NO:10 and SEQ ID NO:11; and the at least one probe is selected from the group consisting of SEQ ID No:12 and oligonucleotide sequences that are at least 70% homologous to SEQ ID NO:12.

29. The kit of claim 28, wherein the oligonucleotide primers consist of SEQ ID NO:10 and SEQ ID NO:11, and the oligonucleotide probe consists of SEQ ID NO:12.

30. The kit of claim 22, wherein the primers and probes target the nucleotides of SEQ ID NO:2 at the location between about base pairs 1966-2073 of the pmpA gene.

31. The kit of claim 22, wherein the detectable label is fluorescence marker.

32. The kit of claim 22, wherein the primer and probes are provided in liquid or dried format.

33. The kit of claim 22, further comprising reagents for performing polymerase chain reaction.

* * * * *

SEQUENCE LISTING

<160> NUMBER OF SEQ ID NOS: 16

<210> SEQ ID NO 1
<211> LENGTH: 2928
<212> TYPE: DNA
<213> ORGANISM: Chlamydia trachomatis
<220> FEATURE:
<221> NAME/KEY: misc_feature
<222> LOCATION: (1)..(2928)
<223> OTHER INFORMATION: Chlamydia Trachomatis strain TW-448
    polymorphic protein A (pmpA) gene
<300> PUBLICATION INFORMATION:
<308> DATABASE ACCESSION NUMBER: NCBI Assession AY884095

<400> SEQUENCE: 1

| | | | | | |
|---|---|---|---|---|---|
| atgaatcgag | ttatagaaat | ccatgctcac | tacgatcaaa | gacaactttc | tcaatctcca | 60 |
| aatacaaact | tcttagtaca | tcatccttat | cttactctta | tcccaagtt | tctactagga | 120 |
| gctctaatct | tctatgctcc | ttattcgttt | gcagaaatgg | aattagctat | ttctggacat | 180 |
| aaacaaggta | aagatcgaga | tacctttacc | atgatctctt | cctgtcctga | aggcactaat | 240 |
| tacatcatca | atcgcaaact | catactcagt | gatttctcgt | tactaaataa | agtttcatca | 300 |
| gggggagcct | ttcggaatct | agcagggaaa | atttccttct | taggaaaaaa | ttcttctgcg | 360 |
| tccattcatt | ttaaacacat | taatatcaat | ggttttggag | ccggagtctt | ttctgaatcc | 420 |
| tctattgaat | ttactgattt | acgaaaactt | gttgcttttg | gatctgaaag | cacaggagga | 480 |
| atttttactg | cgaaagagga | catctctttt | aaaaacaacc | accacattgc | cttccgcaat | 540 |
| aatatcacca | agggaatgg | tggcgttatc | cagctccaag | gagatatgaa | aggaagcgta | 600 |
| tcctttgtag | atcaacgtgg | agctatcatc | tttaccaata | accaagctgt | aacttcttca | 660 |
| tcaatgaaac | atagtggtcg | tggaggagca | attagcggtg | acttcgcagg | atccagaatt | 720 |
| cttttttctta | ataaccaaca | aattactttc | gaaggcaata | gcgctgtgca | tggaggtgct | 780 |
| atctacaata | agaatggcct | tgtcgagttc | ttaggaaatg | caggacctct | tgccttaaa | 840 |
| gagaacacaa | caatagctaa | cgggggagct | atatacacaa | gtaatttcaa | agcgaatcaa | 900 |
| caaacatccc | ccattctatt | ctctcaaaat | catgcgaata | agaaaggcgg | agcgatttac | 960 |
| gcgcaatatg | tgaacttaga | acagaatcaa | gatactattc | gctttgaaaa | aaataccgct | 1020 |
| aaagaaggcg | gtggagccat | cacctcttct | caatgctcaa | ttactgctca | taataccatc | 1080 |
| acttttccg | ataatgctgc | cggagatctt | ggaggaggag | caattcttct | agaagggaaa | 1140 |
| aaaccttctc | taaccttgat | tgctcatagt | ggtaatattg | catttagcgg | caataccatg | 1200 |
| cttcatatca | ccaaaaaagc | ttccctagat | cgacacaatt | ctatcttaat | caagaagct | 1260 |
| ccctataaaa | tccaacttgc | agcgaacaaa | aaccattcta | ttcatttctt | tgatcctgtc | 1320 |
| atggcattgt | cagcatcatc | ttcccctata | caaatcaatg | ctcctgagta | tgaaactccc | 1380 |
| ttcttctcac | ctaagggtat | gatcgttttc | tcgggtgcga | atctttttaga | tgatgctagg | 1440 |
| gaagatgttg | caaatagaac | atcgattttt | aaccaacccg | ttcatctata | taatggcacc | 1500 |
| ctatctatcg | aaaatggagc | ccatctgatt | gtccaaagct | tcaaacagac | cggaggacgt | 1560 |
| atcagtttat | ctccaggatc | ctccttggct | ctatacacga | tgaactcgtt | cttccatggc | 1620 |
| aacatatcca | gcaagaacc | cctagaaatt | aatggttaa | gctttggagt | agatatctct | 1680 |
| ccttctaatc | ttcaagcaga | gatccgtgcc | ggcaacgctc | ctttacgatt | atccggatcc | 1740 |
| ccatctatcc | atgatcctga | aggattattc | tacgaaaatc | gcgatactgc | agcatcacca | 1800 |
| taccaaatgg | aaatcttgct | cacctctgat | aaaactgtag | atatctccaa | atttactact | 1860 |

-continued

```
gattctctag ttacgaacaa acaatcagga ttccaaggag cctggcattt tagctggcag 1920
ccaaatacta taaacaatac taaacaaaaa atattaagag cttcttggct cccaacagga 1980
gaatatgtcc ttgaatccaa tcgagtgggg cgtgccgttc ctaattcctt atggagcaca 2040
tttttacttt tacagacagc ctctcataac ttaagcgatc atctatgtaa taatcgatct 2100
cttattccta cttcatactt cggagtttta attggaggaa ctggagcaga aatgtctacc 2160
cactcctcag aagaagaaag ttttatatct cgtttaggag ctacaggaac ctctatcata 2220
cgcttaactc cctccctgac actctctgga ggaggctcac atatgttcgg agattcgttc 2280
gttgcagact taccagaaca catcacttca gaaggaattg ttcagaatgt cggtttaacc 2340
catgtctggg gaccccttac tgtcaattct acattatgtg cagccttaga tcacaacgcg 2400
atggtccgca tatgctccaa aaaagatcac acctatggga aatgggatac attcggtatg 2460
cgaggaacat taggagcctc ttatacattc ctagaatatg atcaaactat gcgcgtattc 2520
tcattcgcca acatcgaagc cacaaatatc ttgcaaagag cttttactga aacaggctat 2580
aacccaagaa gtttttccaa gacaaaactt ctaaacatcg ccatccccat agggattggt 2640
tatgaattct gcttagggaa tagctctttt gctctactag gtaagggatc catcggttac 2700
tctcgagata ttaaacgaga aaacccatcc actcttgctc acctggctat gaatgatttt 2760
gcttggacta ccaatggctg ttcagttcca acctctgcac acacattggc aaatcaattg 2820
attcttcgct ataaagcatg ttccttatac atcacggcat atactatcaa ccgtgaaggg 2880
aagaacctct ccaatagctt atcctgcgga ggctatgttg gcttctaa 2928
```

<210> SEQ ID NO 2
<211> LENGTH: 342
<212> TYPE: DNA
<213> ORGANISM: Chlamydia trachomatis
<220> FEATURE:
<221> NAME/KEY: misc_feature
<222> LOCATION: (1)..(342)
<223> OTHER INFORMATION: Target segment corresponding to locations 1835-2176 of the C. trachomatis pmpA gene

<400> SEQUENCE: 2

```
ctgtagatat ctccaaattt actactgatt ctctagttac gaacaaacaa tcaggattcc 60
aaggagcctg gcattttagc tggcagccaa atactataaa caatactaaa caaaaaaatat 120
taagagcttc ttggctccca acaggagaat atgtccttga atccaatcga gtggggcgtg 180
ccgttcctaa ttccttatgg agcacatttt tacttttaca gacagcctct cataacttaa 240
gcgatcatct atgtaataat cgatctctta ttcctacttc atacttcgga gttttaattg 300
gaggaactgg agcagaaatg tctacccact cctcagaaga ag 342

<210> SEQ ID NO 3
<211> LENGTH: 21
<212> TYPE: DNA
<213> ORGANISM: Chlamydia trachomatis
<220> FEATURE:
<221> NAME/KEY: misc_feature
<222> LOCATION: (1)..(21)
<223> OTHER INFORMATION: pmpA primer binding site corresponding to locations 1966-1986 of the C. trachomatis pmpA gene
<400> SEQUENCE: 3
atattctcct gttgggagcc a 21

<210> SEQ ID NO 4
<211> LENGTH: 24
```

```
<212> TYPE: DNA
<213> ORGANISM: Chlamydia trachomatis
<220> FEATURE:
<221> NAME/KEY: misc_feature
<222> LOCATION: (1)..(24)
<223> OTHER INFORMATION: pmpA primer binding site corresponding to
      locations 2020-2043 of the C. trachomatis pmpA gene

<400> SEQUENCE: 4
cctaattcct tatggagcac attt                                            24

<210> SEQ ID NO 5
<211> LENGTH: 19
<212> TYPE: DNA
<213> ORGANISM: Chlamydia trachomatis
<220> FEATURE:
<221> NAME/KEY: misc_feature
<222> LOCATION: (1)..(19)
<223> OTHER INFORMATION: pmpA primer binding site corresponding to
      locations 2000-2018 of the C. trachomatis pmpA gene

<400> SEQUENCE: 5
atcgagtggg gcgtgccgt                                                  19

<210> SEQ ID NO 6
<211> LENGTH: 25
<212> TYPE: DNA
<213> ORGANISM: Chlamydia trachomatis
<220> FEATURE:
<221> NAME/KEY: misc_feature
<222> LOCATION: (1)..(25)
<223> OTHER INFORMATION: pmpA primer binding site corresponding to
      locations 1973-1997 of the C. trachomatis pmpA gene

<400> SEQUENCE: 6
gattcaagga catattctcc tgttg                                           25

<210> SEQ ID NO 7
<211> LENGTH: 24
<212> TYPE: DNA
<213> ORGANISM: Chlamydia trachomatis
<220> FEATURE:
<221> NAME/KEY: misc_feature
<222> LOCATION: (1)..(24)
<223> OTHER INFORMATION: pmpA primer binding site corresponding to
      locations 2055-2078 of the C. trachomatis pmpA gene

<400> SEQUENCE: 7
gacagcctct cataacttaa gcga                                            24

<210> SEQ ID NO 8
<211> LENGTH: 28
<212> TYPE: DNA
<213> ORGANISM: Chlamydia trachomatis
<220> FEATURE:
<221> NAME/KEY: misc_feature
<222> LOCATION: (1)..(28)
<223> OTHER INFORMATION: pmpA primer binding site corresponding to
      locations 2013-2040 of the C. trachomatis pmpA gene

<400> SEQUENCE: 8
tgtgctccat aaggaattag gaacggca                                        28

<210> SEQ ID NO 9
<211> LENGTH: 29
<212> TYPE: DNA
<213> ORGANISM: Chlamydia trachomatis
<220> FEATURE:
<221> NAME/KEY: misc_feature
```

-continued

```
<222> LOCATION: (1)..(29)
<223> OTHER INFORMATION: pmpA primer binding site corresponding to
      locations 2045-2073 of the C. trachomatis pmpA gene
<400> SEQUENCE: 9
tacttttaca gacagcctct cataactta 29

<210> SEQ ID NO 10
<211> LENGTH: 21
<212> TYPE: DNA
<213> ORGANISM: Artificial Sequence
<220> FEATURE:
<223> OTHER INFORMATION: Synthetic primer
<400> SEQUENCE: 10
tggctcccaa caggagaata t 21

<210> SEQ ID NO 11
<211> LENGTH: 24
<212> TYPE: DNA
<213> ORGANISM: Artificial Sequence
<220> FEATURE:
<223> OTHER INFORMATION: Synthetic primer
<400> SEQUENCE: 11
aaatgtgctc cataaggaat tagg 24

<210> SEQ ID NO 12
<211> LENGTH: 19
<212> TYPE: DNA
<213> ORGANISM: Artificial Sequence
<220> FEATURE:
<223> OTHER INFORMATION: Synthetic Probe
<400> SEQUENCE: 12
acggcacgcc ccactcgat 19

<210> SEQ ID NO 13
<211> LENGTH: 25
<212> TYPE: DNA
<213> ORGANISM: Artificial Sequence
<220> FEATURE:
<223> OTHER INFORMATION: Synthetic primer
<400> SEQUENCE: 13
caacaggaga atatgtcctt gaatc 25

<210> SEQ ID NO 14
<211> LENGTH: 24
<212> TYPE: DNA
<213> ORGANISM: Artificial Sequence
<220> FEATURE:
<223> OTHER INFORMATION: Synthetic Primer
<400> SEQUENCE: 14
tcgcttaagt tatgagaggc tgtc 24

<210> SEQ ID NO 15
<211> LENGTH: 28
<212> TYPE: DNA
<213> ORGANISM: Artificial Sequence
<220> FEATURE:
<223> OTHER INFORMATION: Synthetic Probe
<400> SEQUENCE: 15
tgccgttcct aattccttat ggagcaca 28
```

```
<210> SEQ ID NO 16
<211> LENGTH: 29
<212> TYPE: DNA
<213> ORGANISM: Artificial Sequence
<220> FEATURE:
<223> OTHER INFORMATION: Synthetic Primer

<400> SEQUENCE: 16
taagttatga gaggctgtct gtaaaagta                                            29
```